United States Patent
Tao et al.

(10) Patent No.: US 6,271,520 B1
(45) Date of Patent: Aug. 7, 2001

(54) ITEM DEFECT DETECTION APPARATUS AND METHOD

(75) Inventors: Yang Tao; Zhiqing Wen, both of Fayetteville, AR (US)

(73) Assignee: University of Arkansas, Little Rock, AR (US)

( * ) Notice: Subject to any disclaimer, the term of this patent is extended or adjusted under 35 U.S.C. 154(b) by 0 days.

(21) Appl. No.: 09/046,270

(22) Filed: Mar. 23, 1998

(51) Int. Cl.[7] .................................................. G01N 23/18
(52) U.S. Cl. ........................ 250/330; 250/910; 250/341.6
(58) Field of Search ................................ 250/910, 341.6, 250/341.8

(56) References Cited

U.S. PATENT DOCUMENTS

| | | | |
|---|---|---|---|
| 2,994,428 | 8/1961 | Daubendick | 209/111.5 |
| 3,563,378 | 2/1971 | Myers | 209/111.7 |
| 3,859,522 | 1/1975 | Cuthbert | 205/223 R |
| 4,244,475 | 1/1981 | Green | 209/588 |
| 4,417,663 | 11/1983 | Suzuki | 209/587 |
| 4,532,723 | 8/1985 | Kellie et al. | 356/73 |
| 5,013,906 | 5/1991 | Miyakawa et al. | 250/223 R |
| 5,197,585 | 3/1993 | Blood | 198/384 |
| 5,339,963 | 8/1994 | Tao | 209/581 |
| 5,397,004 | 3/1995 | Kaiser et al. | 209/577 |
| 5,526,119 | * 6/1996 | Blit et al. | 356/402 |
| 5,533,628 | 7/1996 | Tao | 209/580 |
| 5,621,215 | 4/1997 | Waldroup et al. | 250/461.2 |
| 5,654,977 | * 8/1997 | Morris | 374/4 |
| 5,732,147 | 3/1998 | Tao | 382/110 |
| 5,822,070 | * 10/1998 | Syré | 356/419 |

OTHER PUBLICATIONS

Tao, Yang; Spherical transform of fruit images for on–line defect extraction of mass objects; Optical Engineering vol. 35, No. 2; Feb. 1996; pp. 344–350.

\* cited by examiner

Primary Examiner—Constantine Hannaher
Assistant Examiner—Otilia Gabor
(74) Attorney, Agent, or Firm—Head, Johnson & Kachigian

(57) ABSTRACT

A method and apparatus is provided which incorporates two separate imaging devices, one near-infrared and one mid-infrared imaging device which simultaneously capture images of the passing objects. The background information is removed and images of the objects remain. A spherical optical transform and a defect preservation transform preserve any defect levels on objects and compensate for the non-lambertian gradient reflectance on spherical objects at their curvatures and dimensions. The processed images provided by the mid-infrared camera are subtracted from the images provided by the near-infrared camera to produce an image of just defects which are analyzed to produce the separation or sorting control signals based on defect rejection decisions and user parameters to signal appropriate mechanical actions (driver commands) to separate objects with defects from those that do not contain defects, or to sort or categorize objects based on the amount, type, size, or character of the defects. At least a portion of the exterior surface of each item or object to be inspected must be raised by about 5–15° C. or more so that the cameras can provide an image of a difference in temperature between outer smooth healthy surface and the cavity at the stem-end, the stem, and calyx of an apple or a similar depression, cavity, protrusion, or the like in another object or item. In accordance with one embodiment of the present invention, heated brush rollers are used to quickly heat the exterior of apples passing along a conveyor to provide the necessary change in temperature to allow the cameras to provide an image of defects, stem-end, stem, and/or calyx.

4 Claims, 24 Drawing Sheets

(12 of 24 Drawing Sheet(s) Filed in Color)

ITEM DEFECT DETECTION APPARATUS AND METHOD

STATEMENT REGARDING FEDERALLY SPONSORED RESEARCH OR DEVELOPMENT

This application may be subject to license rights of the U.S. Government and in particular the U.S. Department of Agriculture (USDA).

CROSS-REFERENCE TO RELATED APPLICATIONS

REFERENCE TO A MICROFICHE APPENDIX

Not Applicable.

BACKGROUND OF THE INVENTION

The present invention is directed to an infrared defect inspection system and, more particularly, high speed defect detection utilizing near and mid-infrared imaging, high speed image processing, comparison and contrast, processed image evaluation and characterization, and the development of control signals for sorting or separating objects or items based on the defect determination. More particularly, the present invention relates to methods of near and mid-infrared imaging for defect inspection and fruit stem-end and calyx identification.

U.S. Pat. Nos. 5,339,963 and 5,533,628 each issued to Yang Tao and assigned to Agri-Tech, Incorporated, are each hereby incorporated by reference, and described methods and apparatus for sorting objects by color, and in particular are directed to the sorting of apples. The color sorting apparatus has a singulator section, a color sorter, and a conveyor which drops the sorted objects into appropriate collection bins. The objects for sorting are transported on an endless conveyor through the singulation and color sorting section. An independently adjustable speed belt rotates in the same direction as the wheels and operates to provide a view of each of the four sides of the object to an imaging device such as a camera which supplies red, green and blue signals to an image processor which performs a color transformation and obtains a single composite hue value for each object or piece of fruit to be sorted. Based on a comparison of the hue value to the user program grading criteria, signals are provided to the conveyor so that the objects are ultimately deposited in the appropriate sorting bins.

Allowed U.S. patent application Ser. No. 08/483,962 filed Jun. 7, 1995, and U.S. Pat. No. 5,732,147 on Mar. 24, 1998 is hereby incorporated by reference and describes an image processing system using cameras and image processing techniques to identify undesirable objects on roller conveyor lines. The cameras above the conveyor capture images of the passing objects (such as apples). The roller background information is removed and images of the objects remain. To analyze each individual object accurately, the adjacent objects are isolated and small noisy residue fragments are removed. A spherical optical transformation and a defect preservation transformation preserve any defect levels on objects even below the roller background and compensate for the non-lambertian gradient reflectants on spherical objects at their curvatures and dimensions. Defect segments are then extracted from the resulting transformed images. The size, level and pattern of the defect segments indicate the degree of defects in the object. The extracted features are fed into a recognition process in a decision-making system for grade rejection decisions. The locations and coordinates of the defects generated by defect allocation function are combined with defect rejection decisions and user parameters to signal appropriate mechanical actions such as to separate objects with defects from those that do not contain defects.

Conventional attempts at using laser scanning and reflectance to detect line shifts or changes in height of the object in order to attempt to detect defects in fruit or other objects have not been successful and are not accurate due to the inability to provide the same orientation of each object, changes in size and shape between individual pieces or items of fruit, and the like.

Still further, it has been difficult to differentiate between true defects such as bruises, limb rub, bulls-eyes, fungus such as black net, blemishes, cuts, injuries, stem punches, cracks, worm holes, insect damage, disease damage, color defects, Russet and the like from the fruit stem-end, stem, calyx, or blossom. Hence, there is a need for an improved method and apparatus for defect detection, apple defect detection as compared to detection of the stem-end, stem, and/or calyx identification, defects in smooth surfaces, and/or defect detection and object or item sorting or separation based thereon.

BRIEF SUMMARY OF THE INVENTION

In accordance with the present invention, a method and apparatus is provided which addresses the drawbacks of the prior art and which incorporates two separate imaging devices, one near-infrared and one mid-infrared imaging device which simultaneously capture images of the passing objects. The background information is removed and images of the objects remain. A spherical optical transform and a defect preservation transform preserve any defect levels on objects and compensate for the non-lambertian gradient reflectants on spherical objects at their curvatures and dimensions.

The mid-infrared or middle infrared camera is used at about 3–5 microns or 8–12 microns to provide an image of the stem-end, stems, and/or calyx but is insensitive to true defects. Near-infrared at about 700–1000 nanometers (nm) is used to provide an image of stem-end, stems, calyx, and defects.

In accordance with the present invention, the processed images provided by the mid-infrared camera are subtracted from the images provided by the near-infrared camera to produce an image of just defects which are analyzed to produce the separation or sorting control signals based on defect rejection decisions and user parameters to signal appropriate mechanical actions (driver commands) to separate objects with defects from those that do not contain defects, or to sort or categorize objects based on the amount, type, size, or character of the defects.

In accordance with the present invention, a complete defect detection system for sorting, separating, or grading apples can be constructed for about $100,000.00 or less. In as much as the present invention is based on the use of infrared imaging devices, such as cameras, the temperature of at least a portion of the exterior surface of each item or object to be inspected must be raised by about 5–15° C. or more so that the cameras can provide an image of a difference in temperature between outer smooth surface and the cavity at the stem-end, the stem, and calyx of an apple or a similar depression, cavity, protrusion, or the like in another object or item. In accordance with one embodiment of the present invention, heated brush rollers are used to quickly heat the exterior of apples passing along a conveyor to provide the necessary change in temperature to allow the cameras to provide an image of defects, stem-end, stem, and/or calyx.

Although the present invention is especially adapted for use in inspecting and detecting defects in apples and other fruits and vegetables such as pears, tomatoes, peaches, apricots, and other stone or pit foods having stems, blossom ends, calyx, or the like, the present invention finds applicability in inspecting and detecting defects in manufactured parts such as cups, dishes, balls, golf balls, bearings, molded plastic items, and the like having smooth surfaces, pits, posts, or the like.

The present invention provides a system which is effective, fast, has high resolution, and which has a greater accuracy and discrimination rate than prior art devices or systems.

The principal object of the present invention is the provision of a method and apparatus for the detection and discrimination of defects in items or objects such as apples.

Another object of the present invention is the provision of a method and apparatus for sorting items or objects based on the character, number, type or aggregation of defects.

A still further object of the present invention is the provision of a method and apparatus for discriminating between stem-end, stems, and calyx as compared to true defects.

Other objects and further scope of the applicability of the present invention will become apparent from the detailed description to follow, taken in conjunction with accompanying drawings wherein like parts are designated by like reference numerals.

BRIEF DESCRIPTION OF THE SEVERAL VIEWS OF THE DRAWING

The file of this patent contains at least one drawing executed in color. Copies of this patent with color drawing (s) will be provided by the Patent and Trademark Office upon request and payment of the necessary fee.

DETAILED DESCRIPTION OF THE INVENTION

Figure 1A:
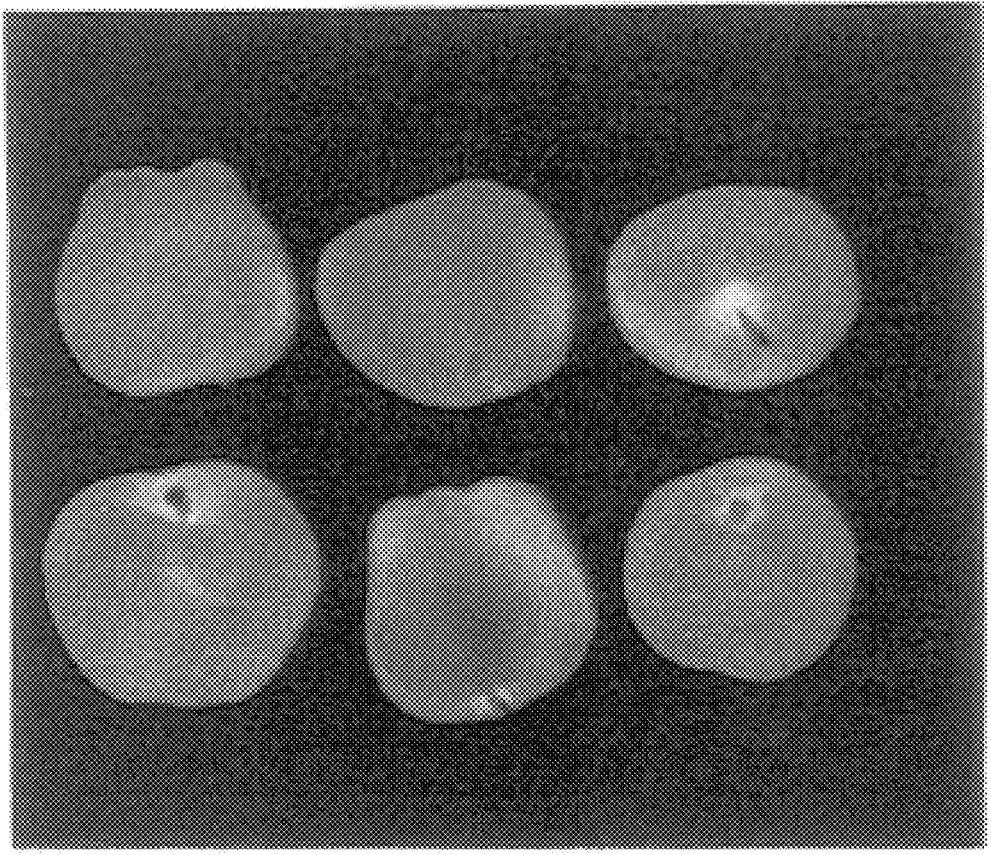
FIGS. 1A–8 are photographic representations or illustrations.

In accordance with the present invention there is provided a method and apparatus utilizing simultaneous mid and near-infrared imaging to detect true defects on items or objects such as fruits and vegetables. The present invention solves the difficult problem that scientists and engineers have been having for more than twenty years of not being able to separate the images of stem-end, stem, and calyx from defects in fruit. In accordance with the present invention, one is able to easily discriminate between true defects and the stem-end, stem and calyx and is also able to accurately inspect both large and small defects.

Since stem-end, stem and calyx appear similar to true defects in images produced by imaging devices such as infrared cameras, they have in the past created tremendous confusion. The near-infrared (NIR) range from about 750 nanometers to 1200 nanometers (nm) is sensitive to defects on fruit. However, near-infrared also picks up stem-end, stem and calyx. Separation of true defects from stem-end, stem, and/or calyx using only near-infrared is very difficult.

In accordance with the present invention, by using mid-infrared (MIR) in the 3 to 12 $\mu$m range (micrometer or micron with the exception of the 5 to 8 $\mu$m range which is sensitive to hot air) which is insensitive to defects but sensitive to stems, stem-end and calyx, one is able to subtract the mid-infrared image from the near-infrared image (NIR-MIR) and obtain an image of only true defects.

Further, since most fruit is stored in controlled atmosphere storage (CA) where the temperature is controlled at about 4° C. typically for fruit like apples, heated brushes such as roller brushes or other types of brushes or rollers which can be heated by hot air, steam, liquid, or other sources, are used to heat the fruit surface sufficiently to provide a change in temperature between the exterior smooth outer surface of the fruit and the stem-end cavity, the calyx, rot, bruise, limb rub, bulls-eyes, fungi such as black net, blemishes, cuts, injuries, stem punches, cracks, worm holes, insect damage, disease damage, color defects such as Russet, and the like which allow the mid-infrared camera to detect stem-end, stems, and calyx and allow the near-infrared to detect stem-end, stem, calyx, and true defects. Although heated brushes are preferred to speed up the process of increasing the temperature of the outer smooth surface of the fruit or other item or object being inspected, exposure to room temperature also enhances the change in temperature or delta-T between the cavities, pits, cracks, stem-end, calyx, stem, and the like with respect to the temperature of the smooth healthy outer surface of the fruit.

The present invention is useful in fruit defect detection, defected fruit sorting, separating, and/or grading, stem-end or calyx identification, cavity spot identification, object detect or deformation identification, and the like.

The present invention is also easily retrofitted to existing or conventional fruit processing and/or packing systems or apparatus. As described in U.S. Pat. Nos. 5,339,963 and 5,533,628 herein incorporated by reference and as described in allowed U.S. patent application Ser. No. 08/483,962 filed Jun. 7, 1995 and to issue as U.S. Pat. No. 5,732,147 on Mar. 24, 1998, also herein incorporated by reference, although some aspects of the fruit packing process are already automated, much of it is still left to manual laborers. The automated equipment that is currently available is generally limited to conveyor systems and systems for measuring the color, size, and weight of apples.

A system manufactured by Agri-Tech, Inc. of Woodstock, Va. automates certain aspects of the apple packing process. At a first point in the packing system, apples are floated in large cleaning tanks. The apples are then elevated out of the tank by conveyors onto an inspection table. Workers alongside the table inspect the apples and eliminate any unwanted defective apples and other foreign material such as leaves, stems, and the like. The remaining apples are then fed on conveyors to cleaning, waxing and drying equipment. After being dried, the apples are sorted according to color, size, and shape and then packaged according to the sort.

As described in U.S. Pat. No. 5,732,147, the inspection process, a key step in the apple packing process, is still conventionally done by hand. Along the apple conveyors in the early cleaning process, workers are positioned to visually inspect the passing apples and remove the apples with defects such as apples with rot, apples that are injured, diseased, or seriously bruised, and other defective apples as well as foreign materials. These undesirable objects especially rotted and diseased apples, must be removed in the early stage (before coating) to prevent contamination of good fruit and reduce cost and successive processing. This manual apple inspection process is labor intensive, difficult, fatiguing, and subject to human error which allows misinspected apples to pass through the line.

Further, apples are graded in part according to the amount and extent of defects. In Washington state, for example, apples with defects are used for processing and to make into applesauce or juice. These apples usually cost less than apples with no defects or only a few defects. Apples that are not used for processing, known as fresh market apples, are also graded on the size of any defects and also on the number of defects.

In accordance with the present invention, an item or object defect identification, inspection, sorting, grading, and separation system is provided which automates the conventional manual inspection process. Further, the present infrared camera system can replace conventional laser inspection and defect detection systems which are more costly, subject to error, and difficult to implement with certain items such as fruit and the like which have irregular contours, shapes, features, and the like. The present method and apparatus does not require that each item or object be oriented similarly to provide for defect detection, inspection, and object grading, sorting, or separation.

Still further, the present invention incorporates patented or state of the art image transformation or processing which transforms a curved or spherical image to a flat image for image discrimination, comparison, subtraction, and the like. As described in an article entitled "Spherical Transform of Fruit Images for On-line Defect Extraction of Mass Objects" in Optical Engineering Vol. 35, No. 2, pgs. 344–350, February, 1996, produced by the Society of Photo-Optical Instrumentation Engineers, and hereby incorporated by reference, Yang Tao describes spherical transform methods developed to solve the problem of detecting defects on spherical curved objects which are difficult to identify because of the object image boundary effect and successfully applies this transform to an automated defect sorter. The spherical transform is obtained by compensating the intensity gradiance on curved objects. Defects below the background level are extracted through a preservation transform. The defect extraction is enabled by a uniformly distributed plain image through 2-step transformations and the defect position is determined by allocation process. The results show the effectiveness of the processing methods for the high-speed on-line defect identification on fruit packing lines.

Figure 1B:
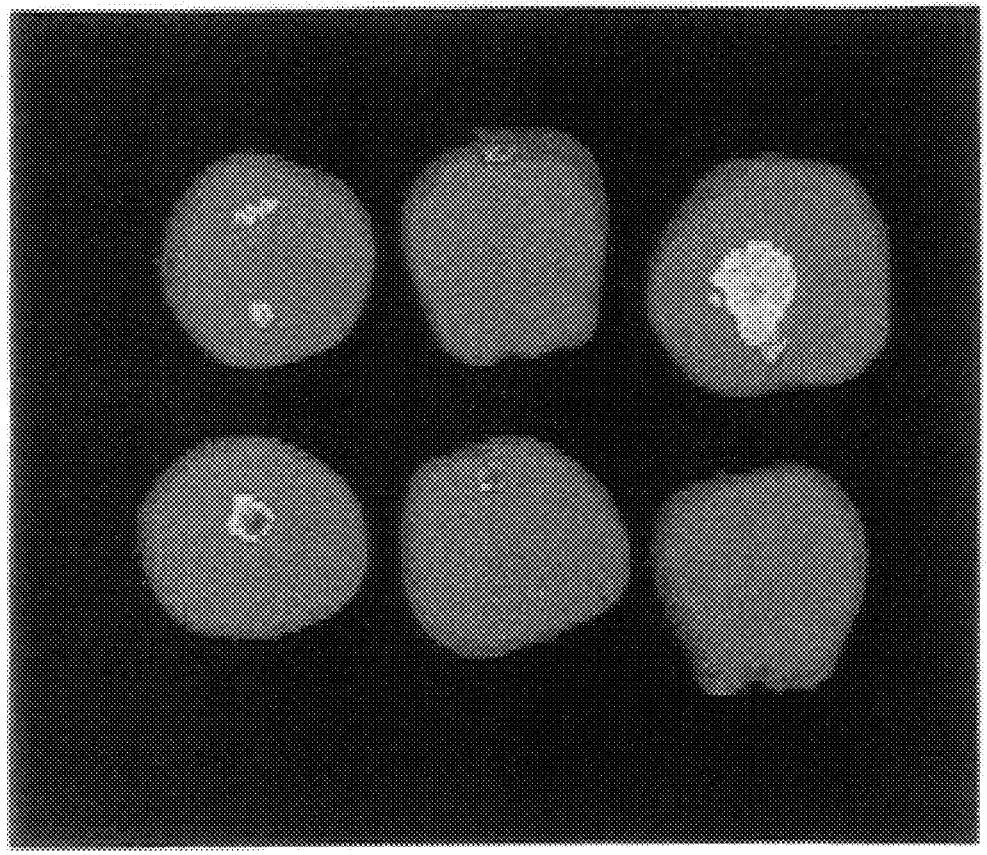
Figure 1C:
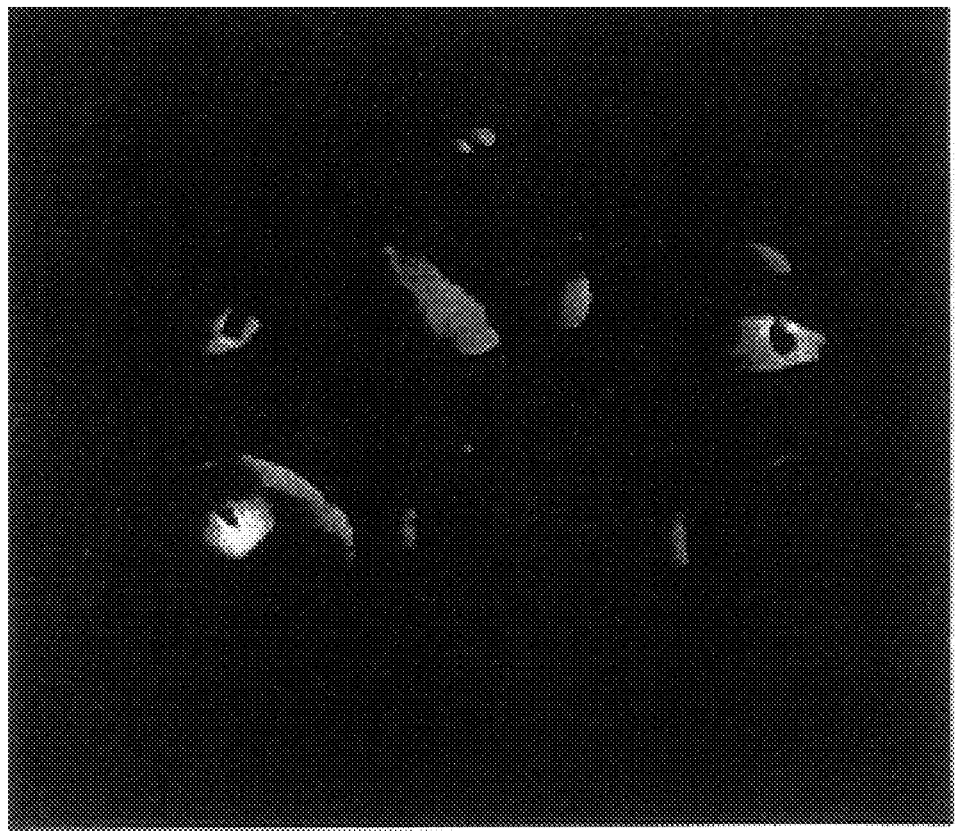
Figure 1D:
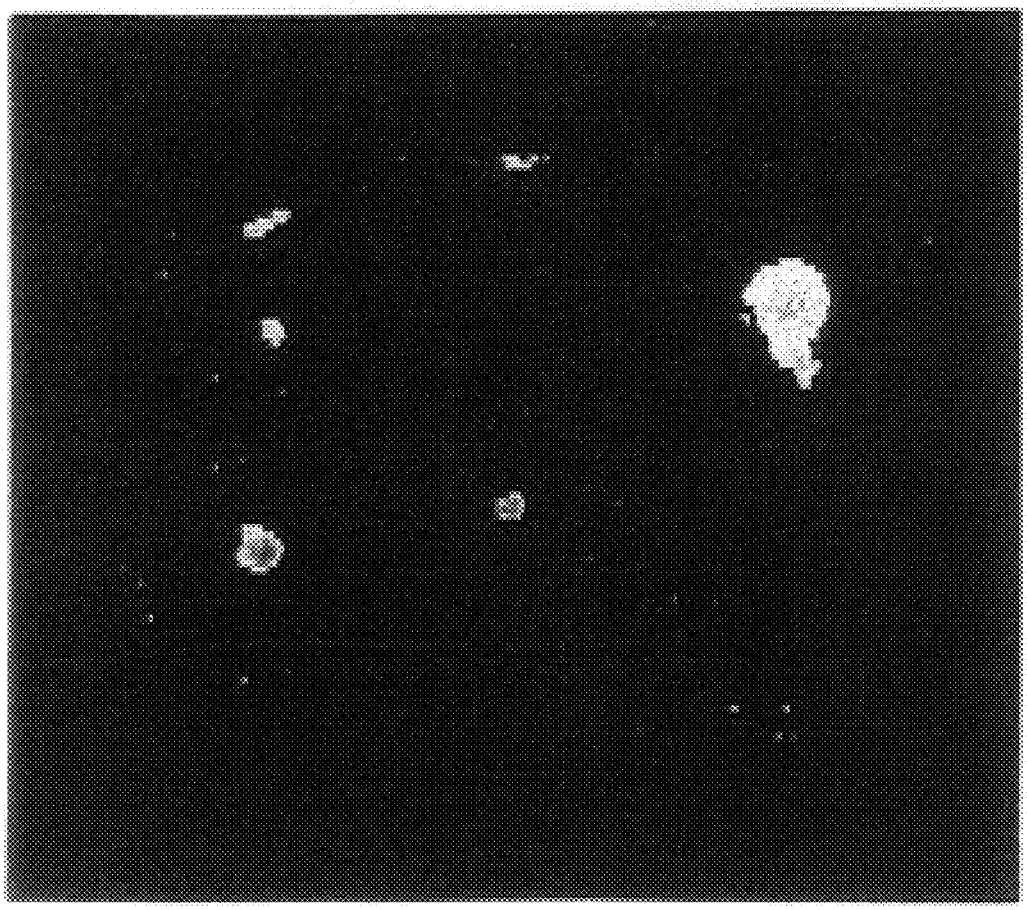

In accordance with the present invention, color images (all gray level red/green) are converted to black and white images which are then compared and contrasted to one another to subtract out the nondefects such as stem-end, stem, and calyx to leave only true defects. As shown in FIGS. 1A–4D of the drawings, simultaneous mid-infrared (MIR) and near-infrared (NIR) images are taken of items or objects such as apples, processed, and then compared to determine if true defects exist. FIG. 1A is a photographic representation of an MIR color image of stem-ends, stems and calyx on apples lying on a conveyor in different orientations. The background image has been eliminated. FIG. 1C is a black and white processed image of FIG. 1A. FIG. 1B is a color NIR image depicting stems, stem-ends, calyx and defects. FIG. 1D is a black and white processed image of FIG. 1B. In accordance with the present invention, FIGS. 1C and 1D are processed, compared, contrasted, the stems, stem-end and calyx of FIG. 1C are subtracted from the image of FIG. 1D and there is left the true defects image which is processed and used to sort, grade, or separate the apples.

Figure 2A:
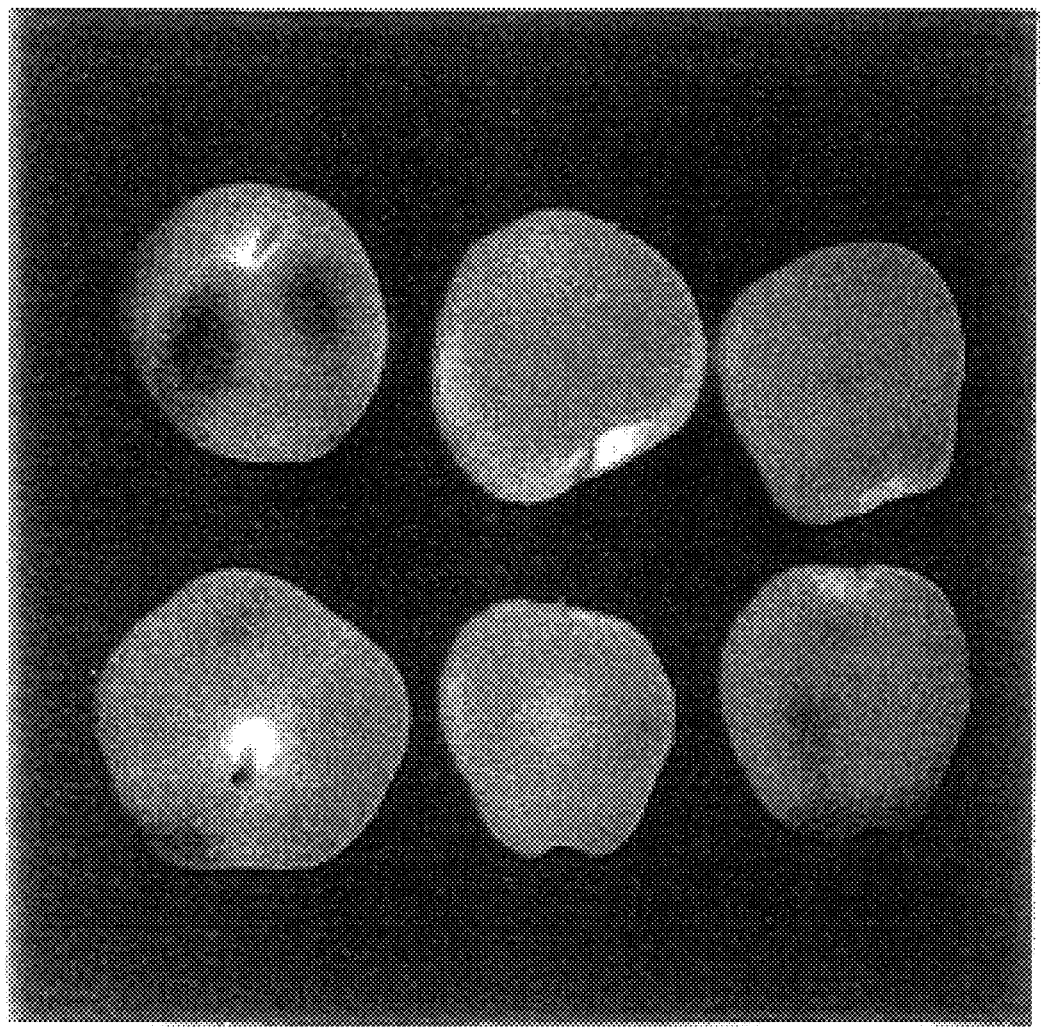
Figure 2B:
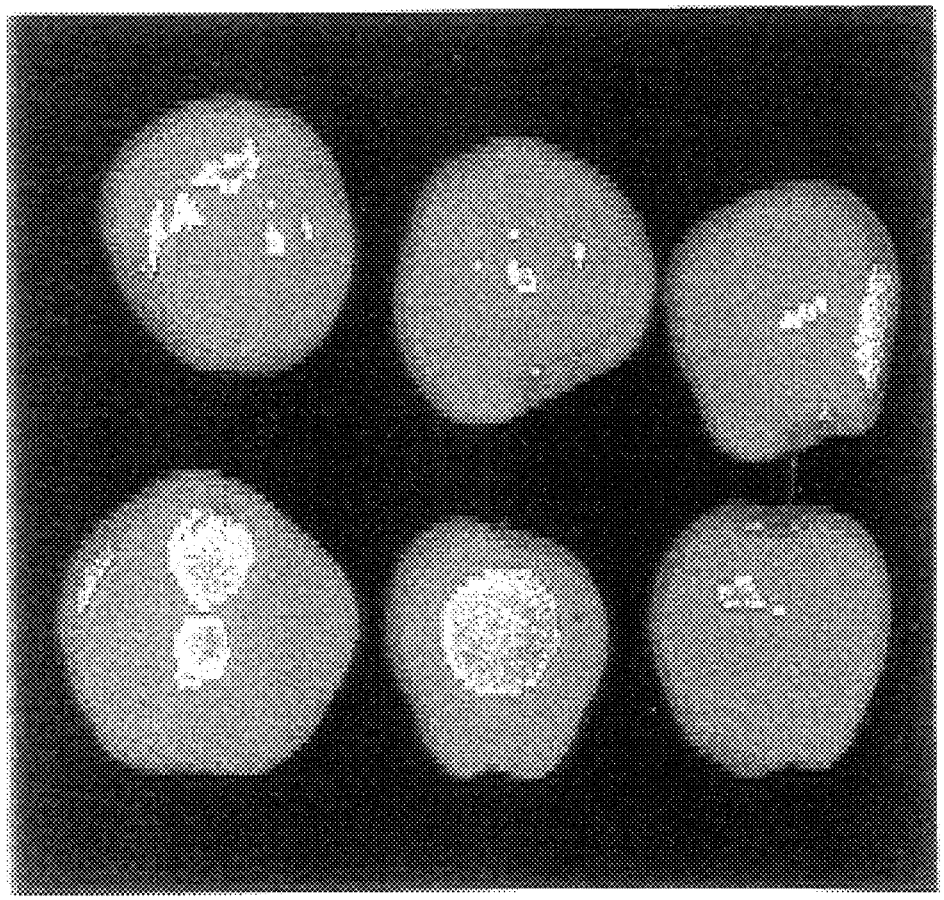
Figure 2C:
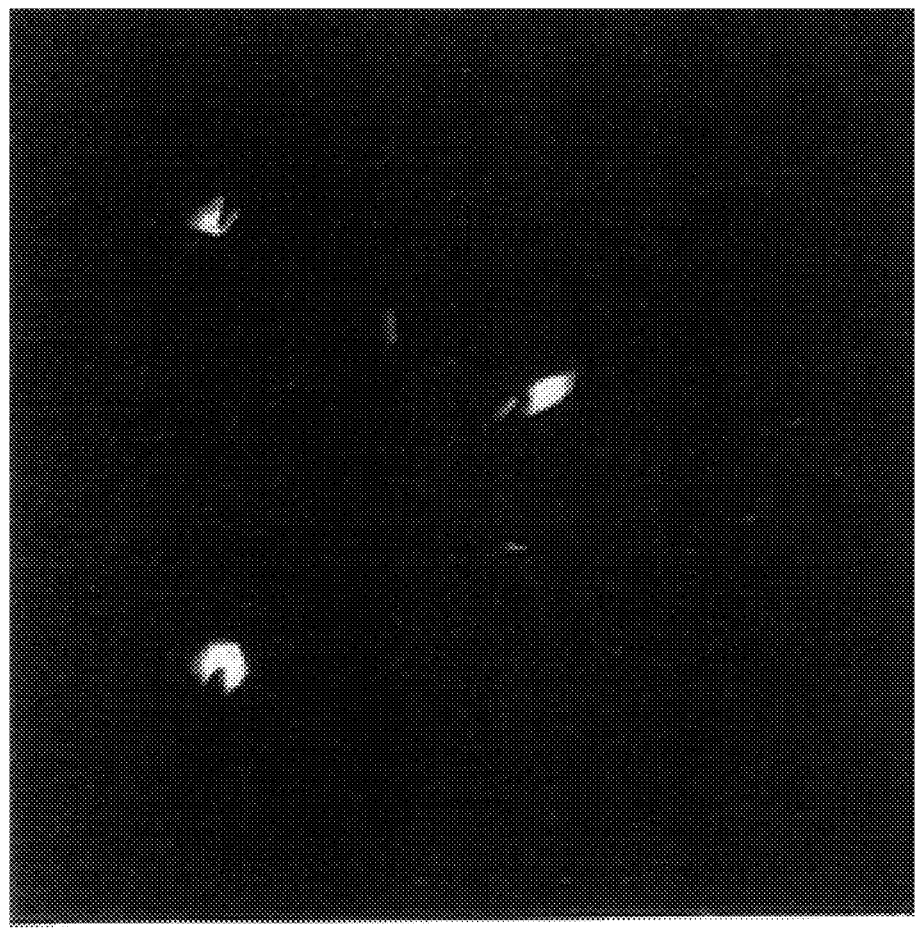
Figure 2D:
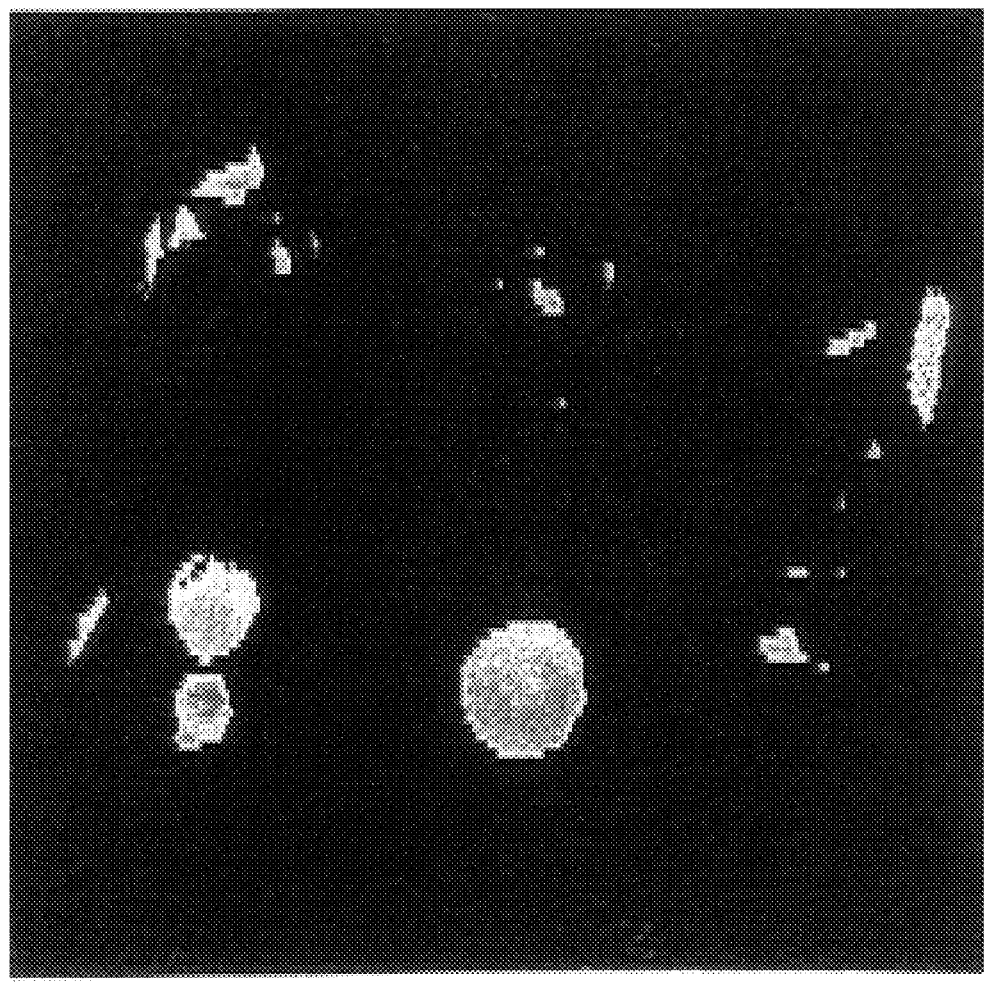

Similarly, FIG. 2A is a color MIR image and FIG. 2C is a black and white processed image from FIG. 2A. FIG. 2B is a color NIR image while FIG. 2D is a black and white processed image of FIG. 2B. Again, FIG. 2C is subtracted from FIG. 2D processed, and the like to determine true defects and which apples are soiled or separated.

Figure 3A:
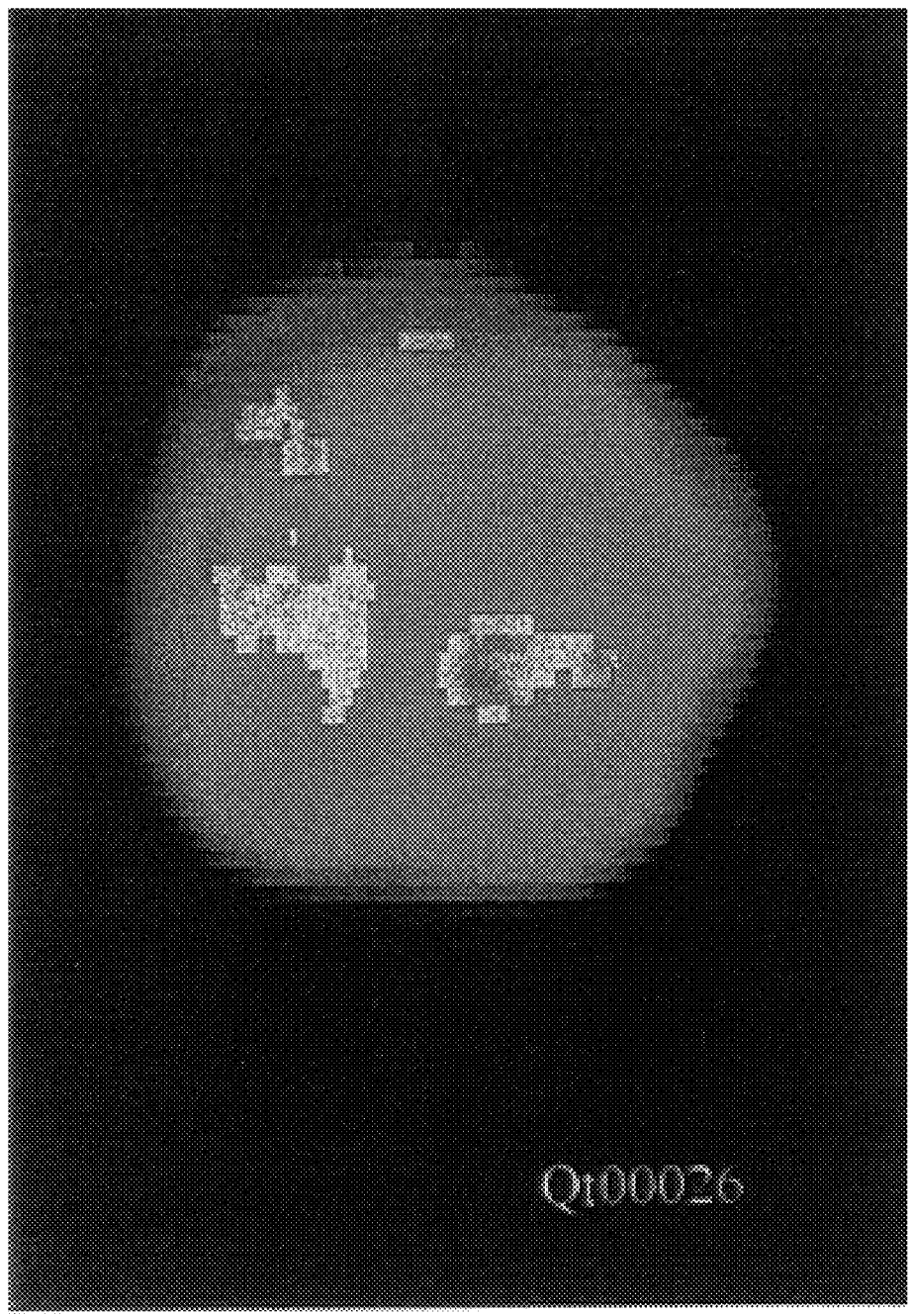
Figure 3B:
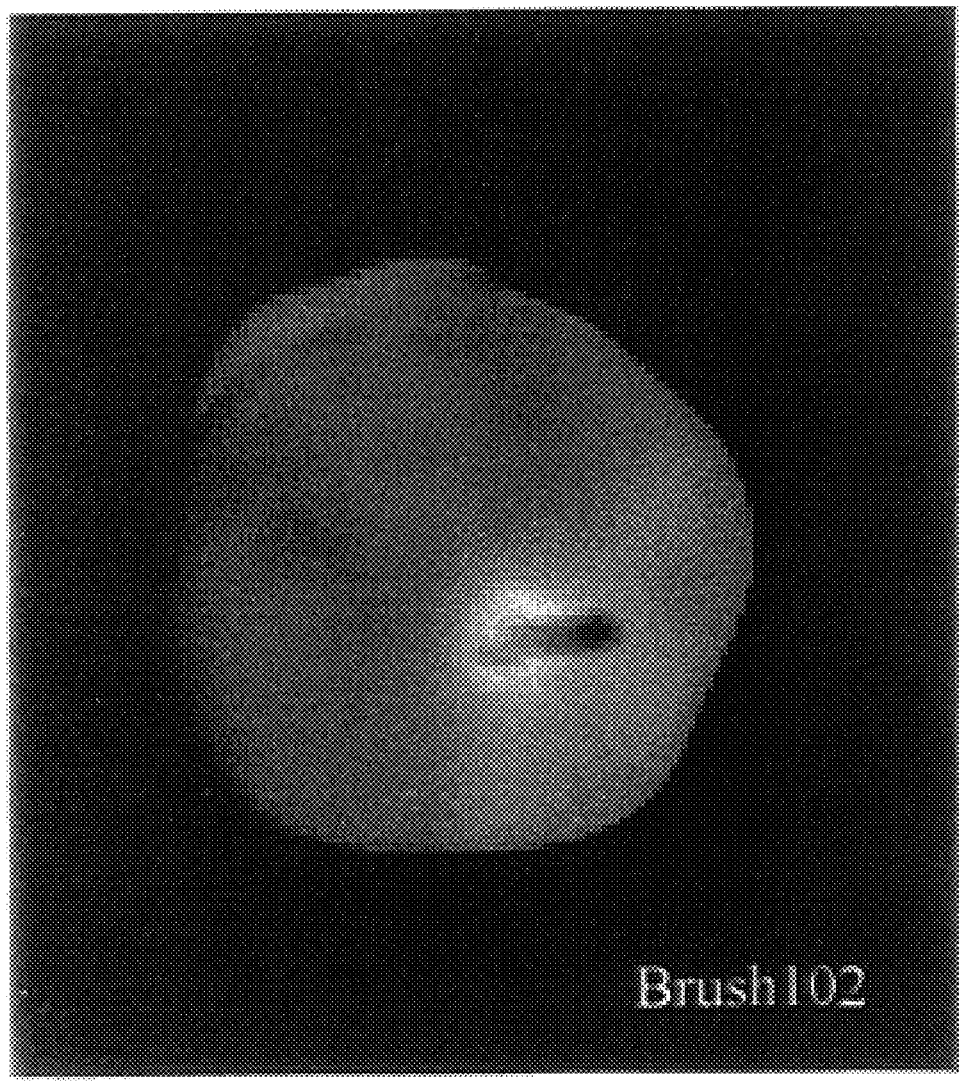
Figure 3C:
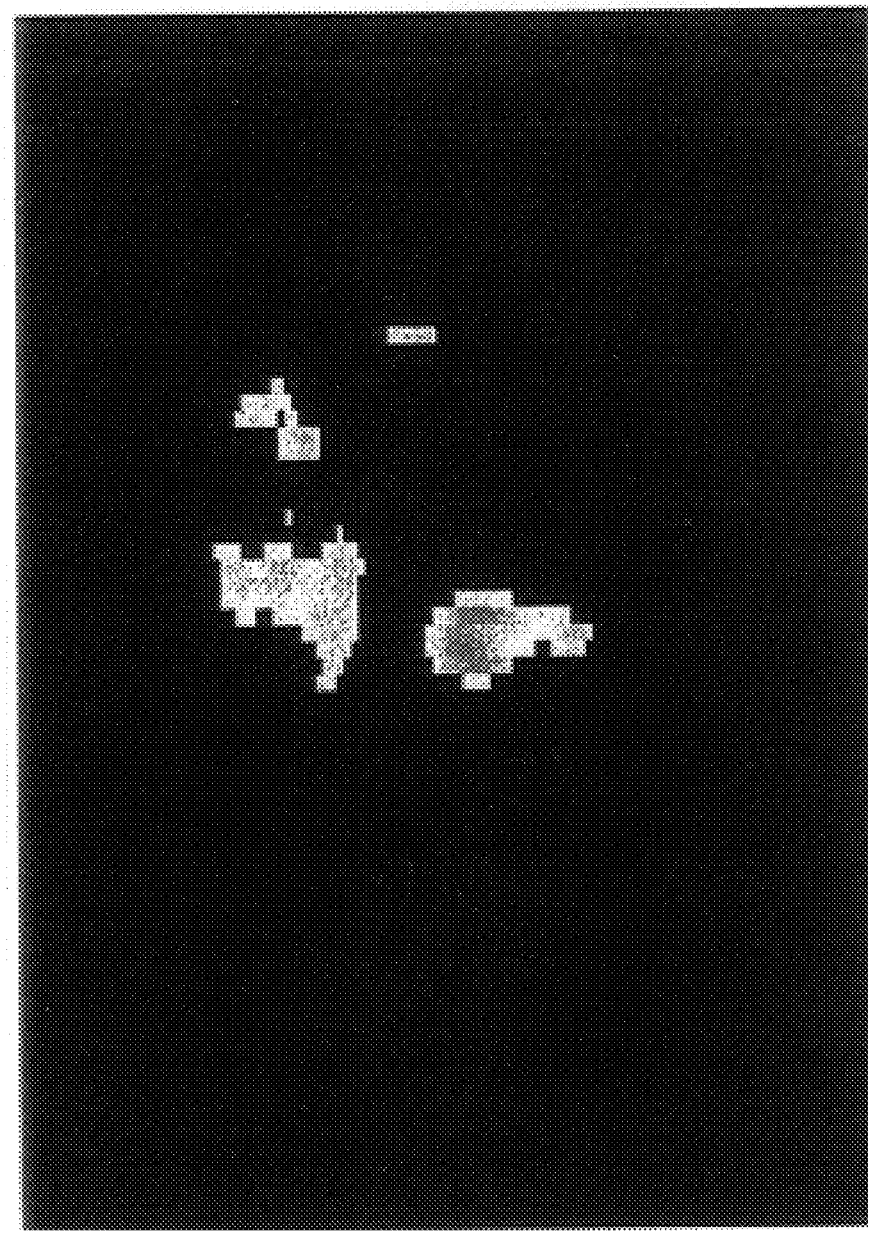
Figure 3D:
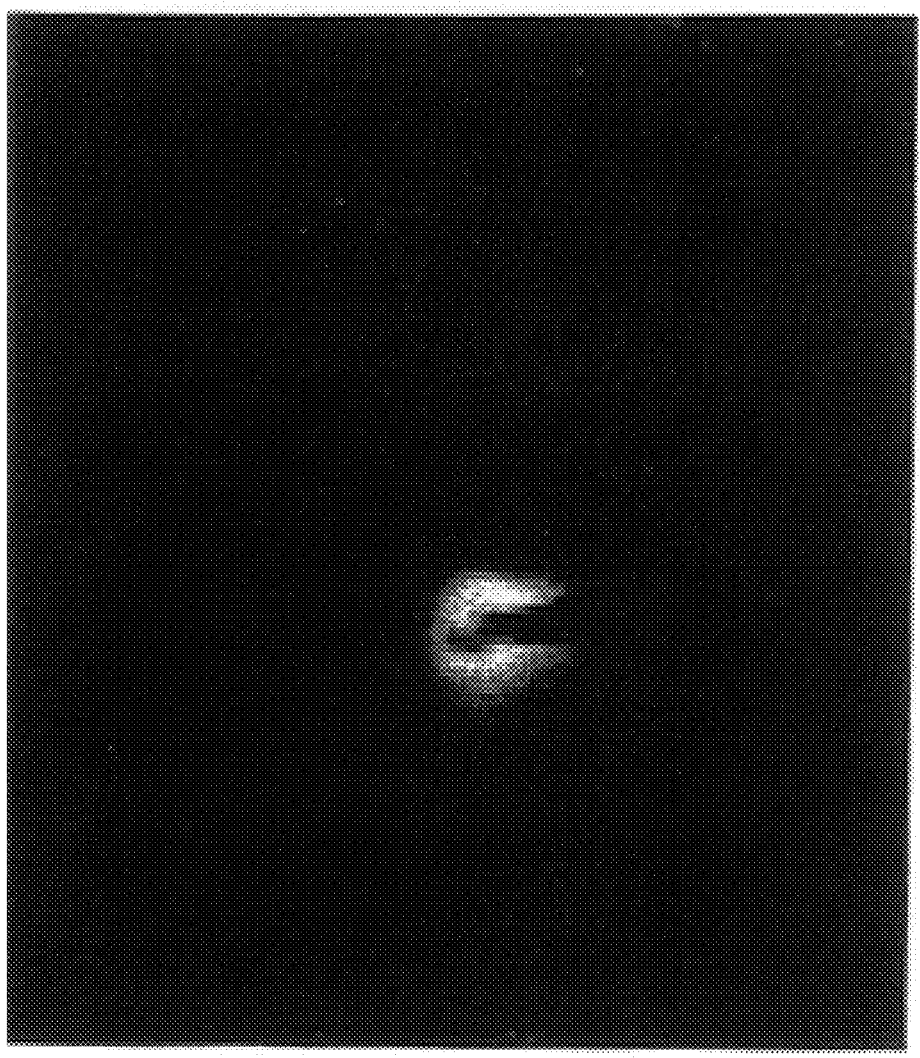
Figure 4A:
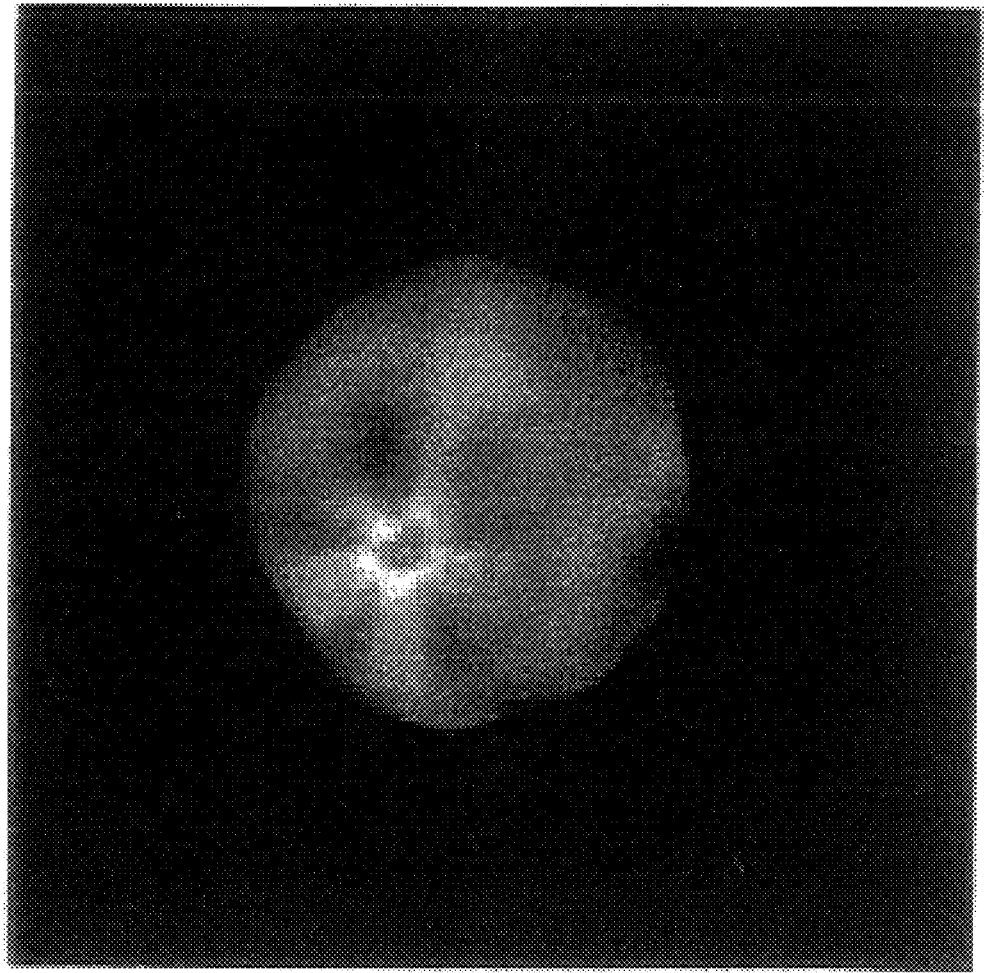
Figure 4B:
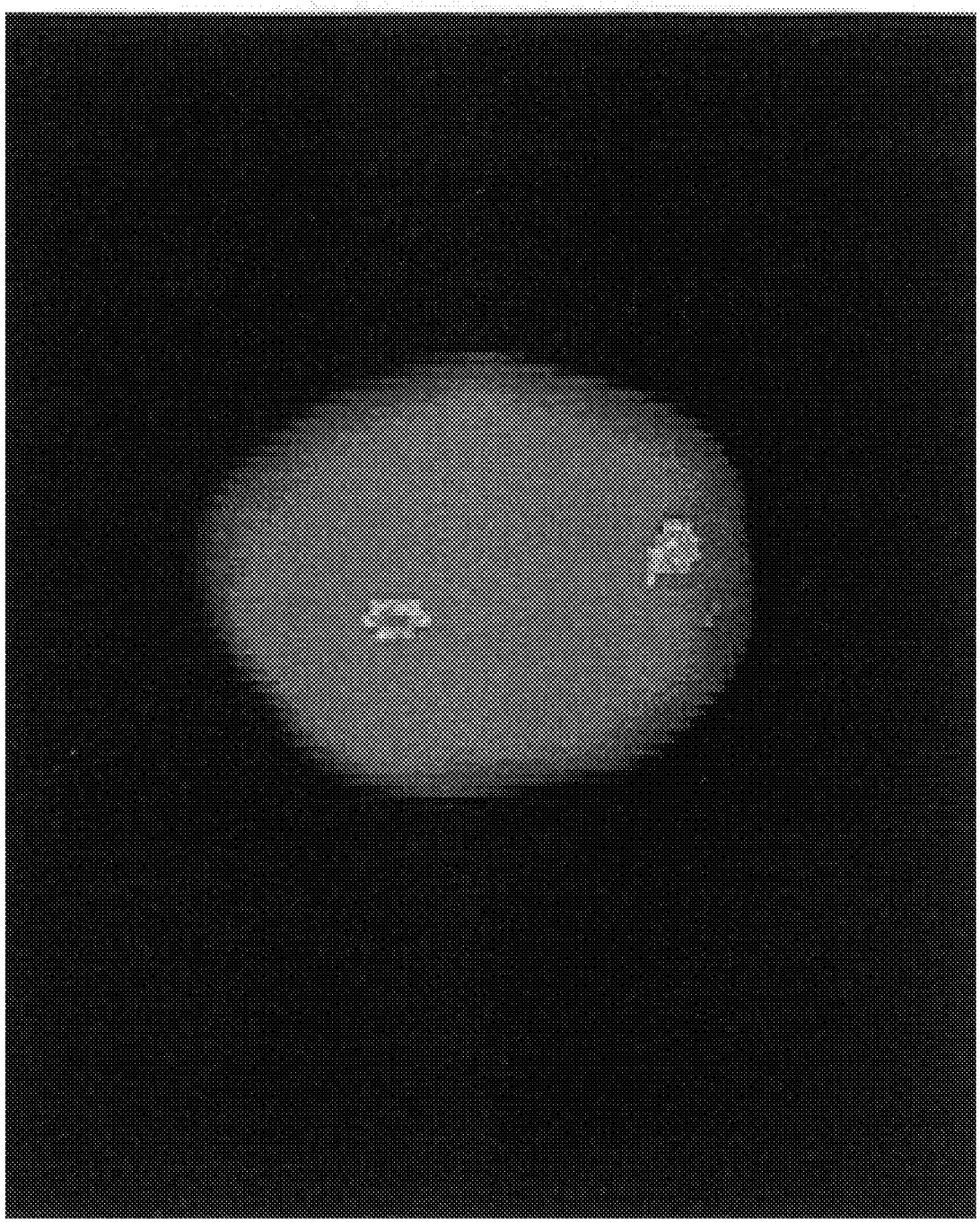
Figure 4C:
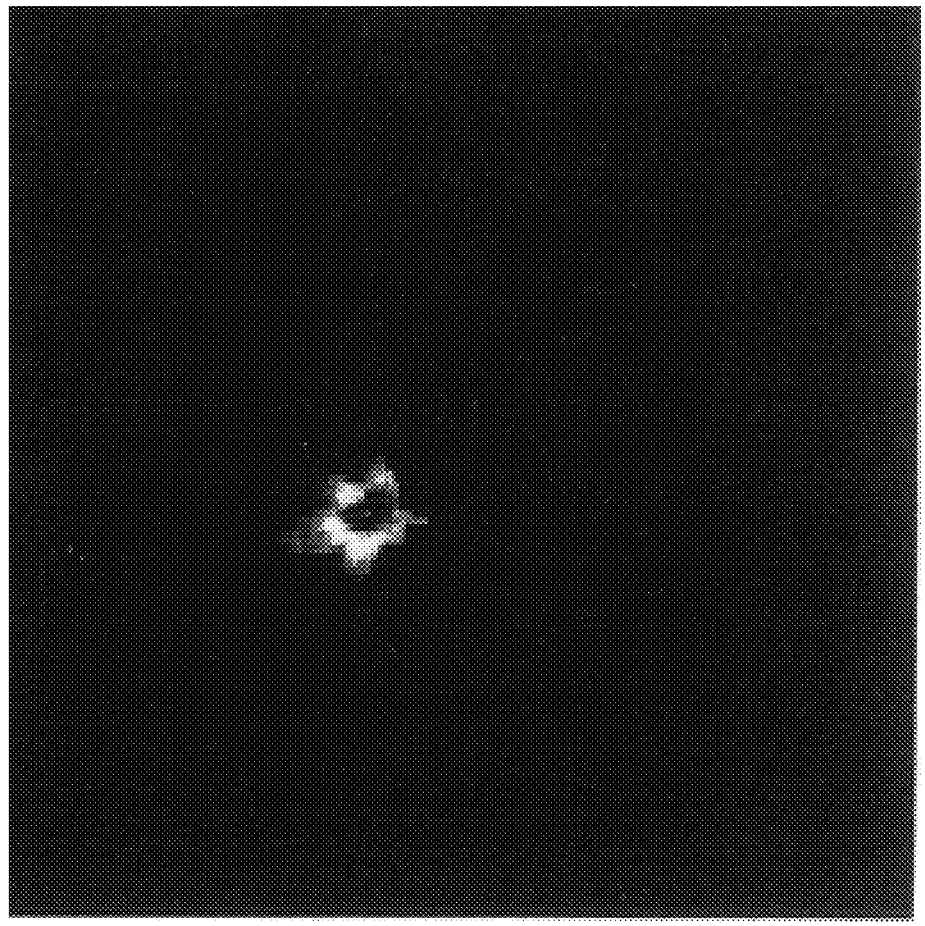
Figure 4D:
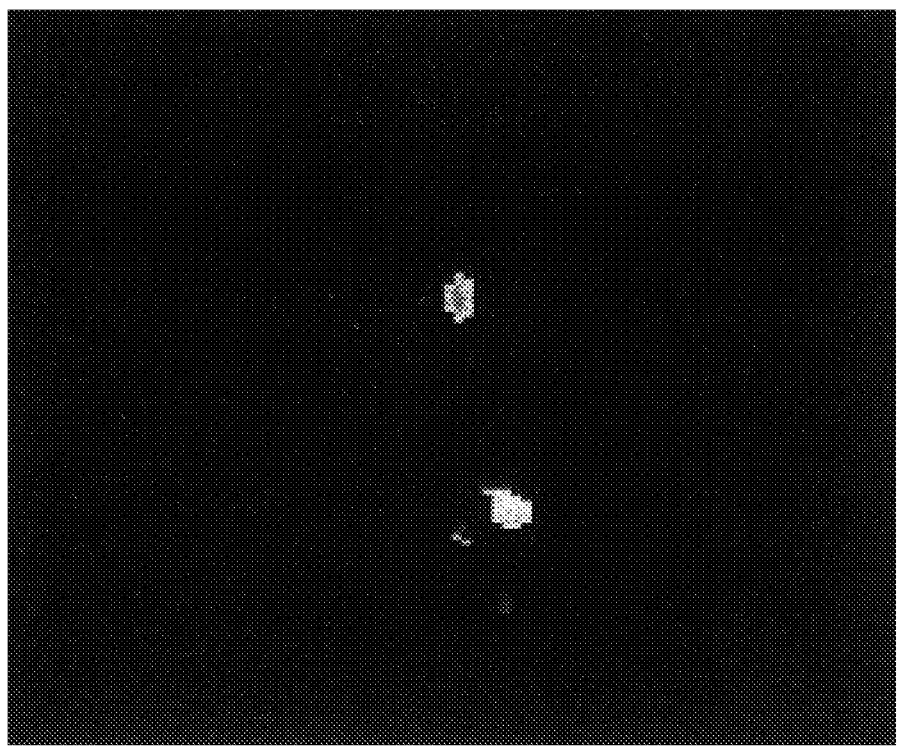
Figure 5:
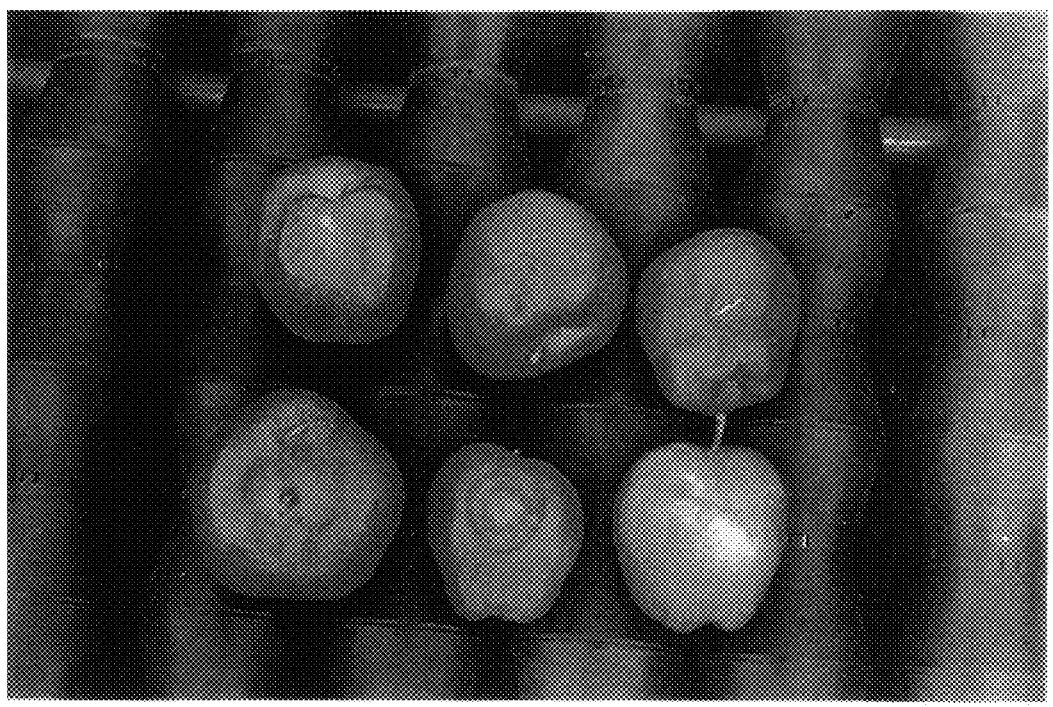
Figure 6:
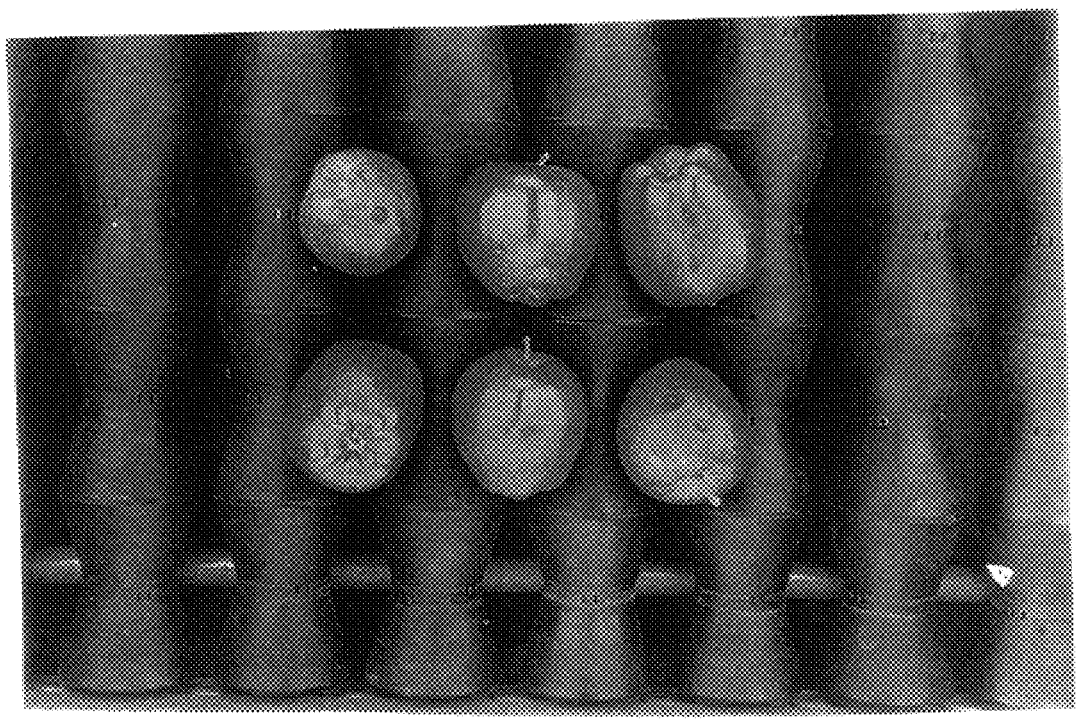
Figure 7:
Figure 8:
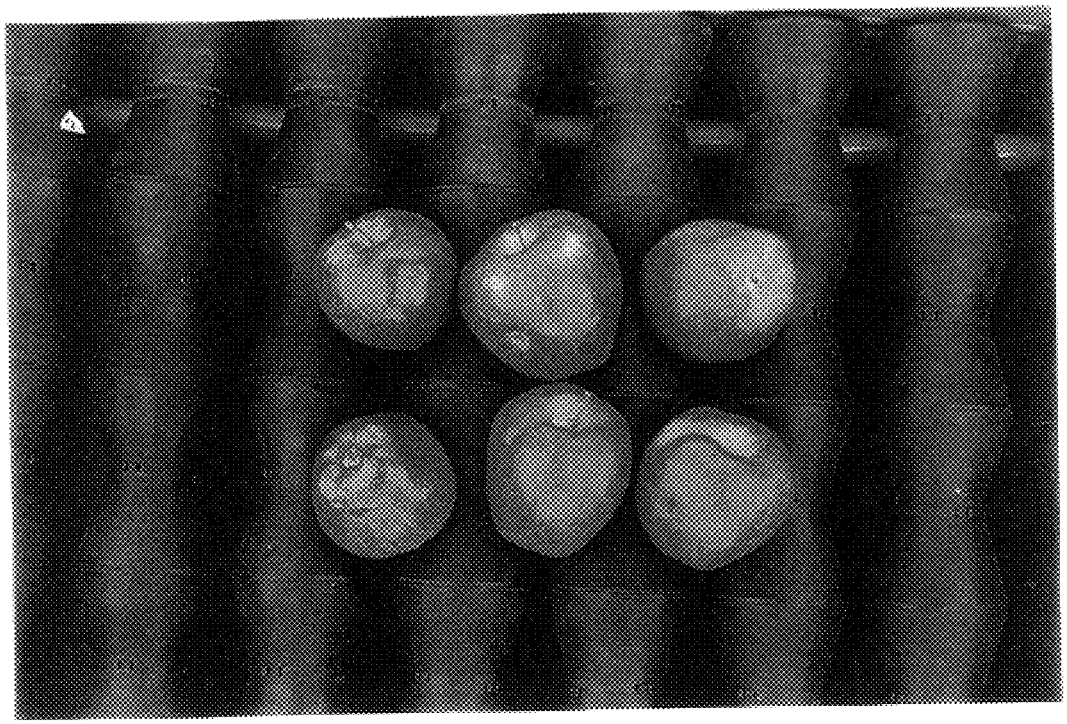

FIGS. 3A–D and FIGS. 4A–D highlight the stem end and calyx respectively of a single apple. FIG. 3A is a color NIR image and FIG. 3C is a black and white processed image of FIG. 3A. FIG. 3B is a color MIR image and FIG. 3D is a processed black and white image of FIG. 3B. FIG. 4A is an MIR image and FIG. 4C is a black and white processed image of FIG. 4A. FIG. 4B is a color NIR image and FIG. 4D is a black and white processed image of FIG. 4B.

FIGS. 5–8 are color photographic representations of different apple orientations on a roller conveyor as well as different true defects and provide a visual appreciation of the difficulty in comparing and contrasting true defects to stems, stem-end, and calyx of an apple or other fruit or vegetable.

Figure 9:
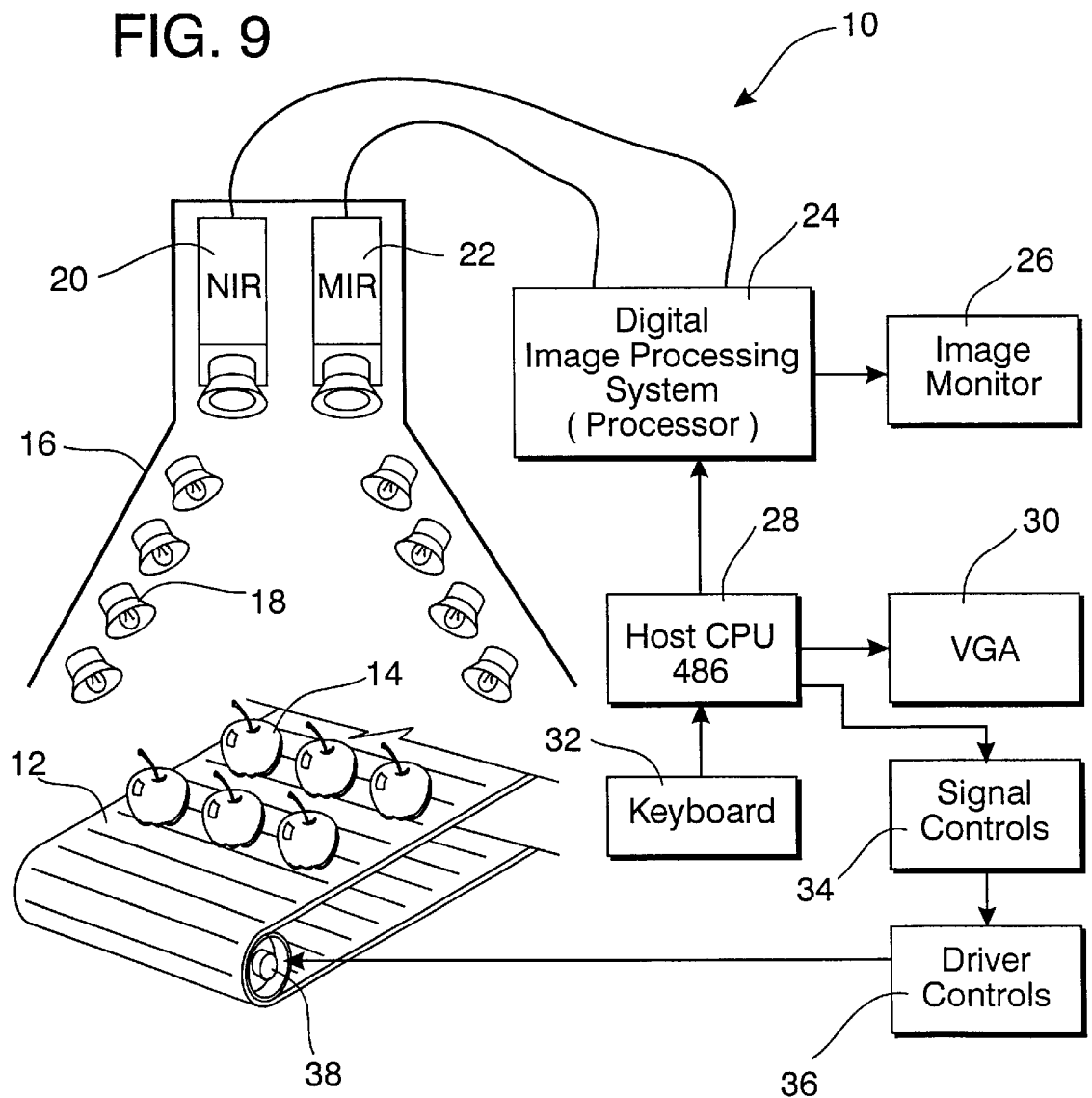
FIGS. 9–12 are schematic diagrams.

FIG. 9 is a schematic representation of a true defect identification and discrimination unit 10 in accordance with an exemplary embodiment of the present invention and including as system hardware a roller conveyor 12 supporting a plurality of apples 14, a light box 16 housing and plurality of lights 18, an NIR camera 20, an MIR camera 22, a digital image processing system or processor 24, an image monitor 26, a host CPU (486 computer) 28, a computer monitor or VGA 30, a computer keyboard 32, signal controls 34, driver controls 36, and a driver, separator, grader, sorter, bin drop control, or the like 38.

Figure 10:
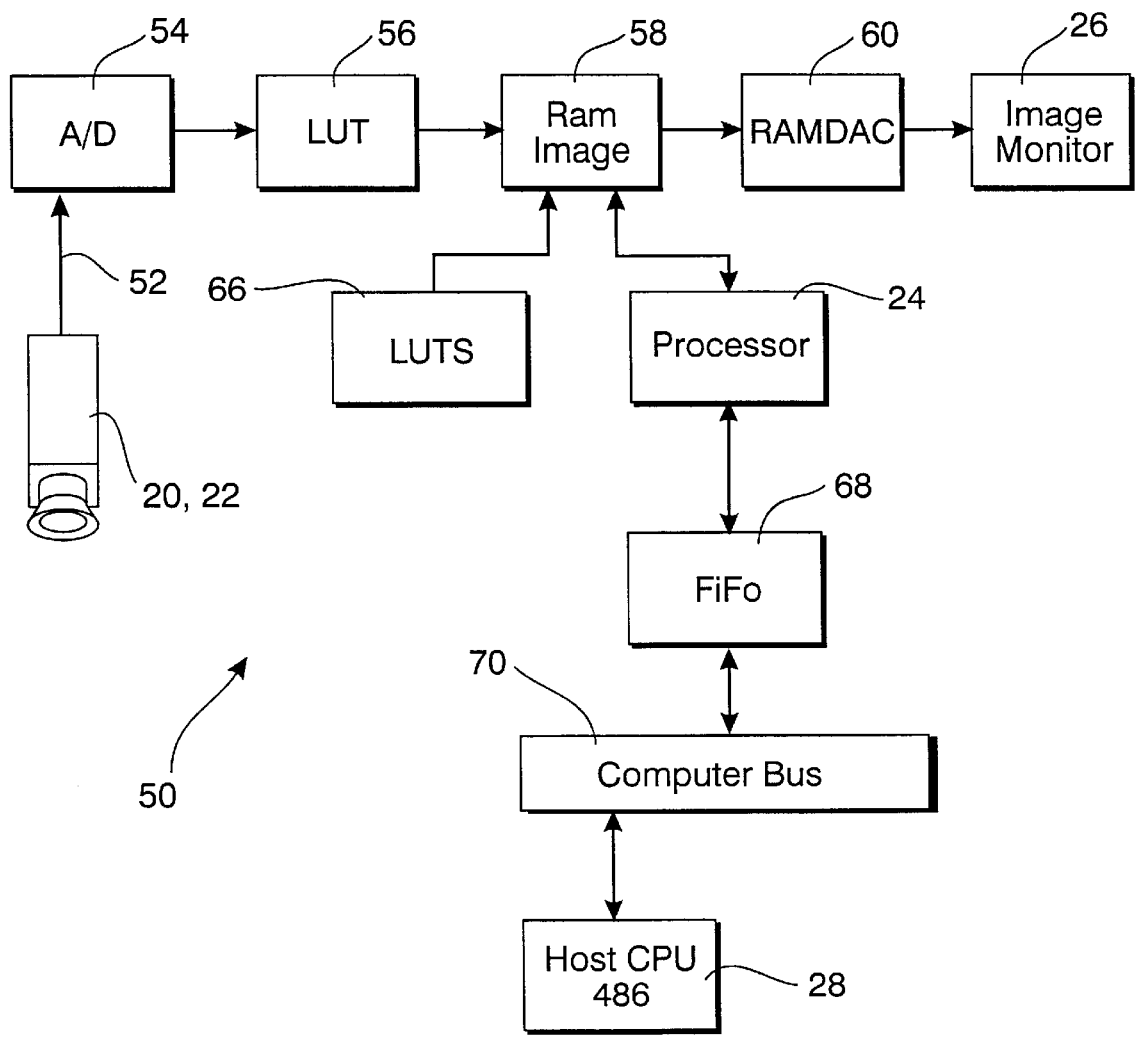

FIG. 10 is a schematic component and process flow diagram showing the processing of each camera image generally designated 50 and shown to include a camera which produces an analog image 52, an A/D analog to digital converter 54, an LUT 56, image ram 58, RAMDAL 60, and image monitor 26. The image ram receives and provides signals to a LUTS 66, and processor 24. The processor 24 receives and provides signals to a FIFO 68 and a computer bus 70 which receives and provides signals to host computer 28.

Figure 11:
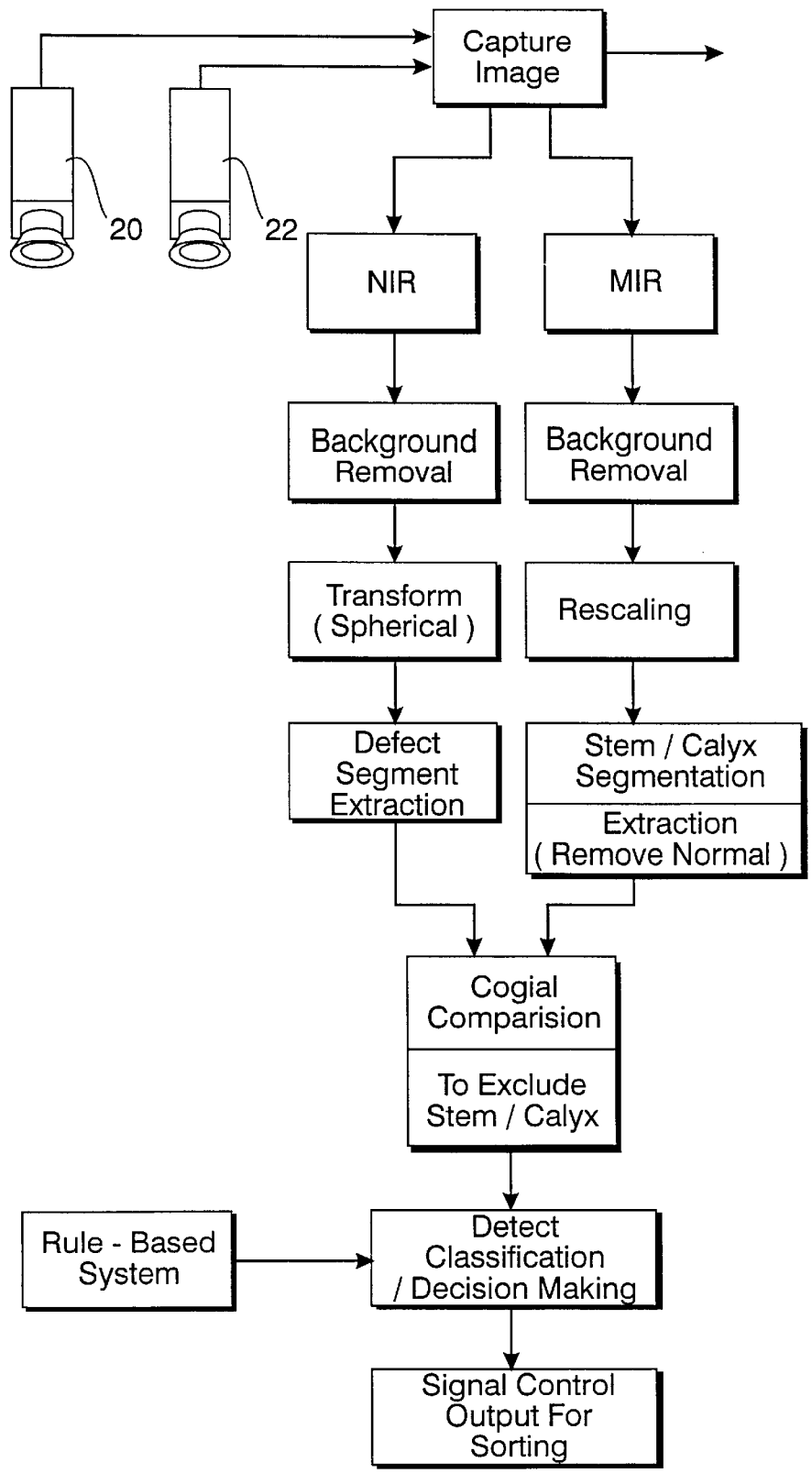

With reference to FIG. 11 there is shown a schematic diagram of the overall procedure or process wherein the images from the cameras 20 and 22 are captured and then the NIR image is processed to remove background, for a spherical transform, defect segment extraction, and the like prior to image comparison. The MIR image from camera 22 has the background removed, spherical transform, is rescaled to provide a common aspect ratio between the cameras and images, and then stem, calyx and defect segmentation and extraction and the like prior to logical comparison. The processed NIR and MIR images are logically compared to exclude stem-end, stem and calyx and then the remaining defects are classified, categorized, and quantified using a rule base system as well as user parameters to provide a control signal for sorting, grading, separating, and the like items or objects such as apples based on the amount, type, quantity, and character of the detected defects.

Figure 12:
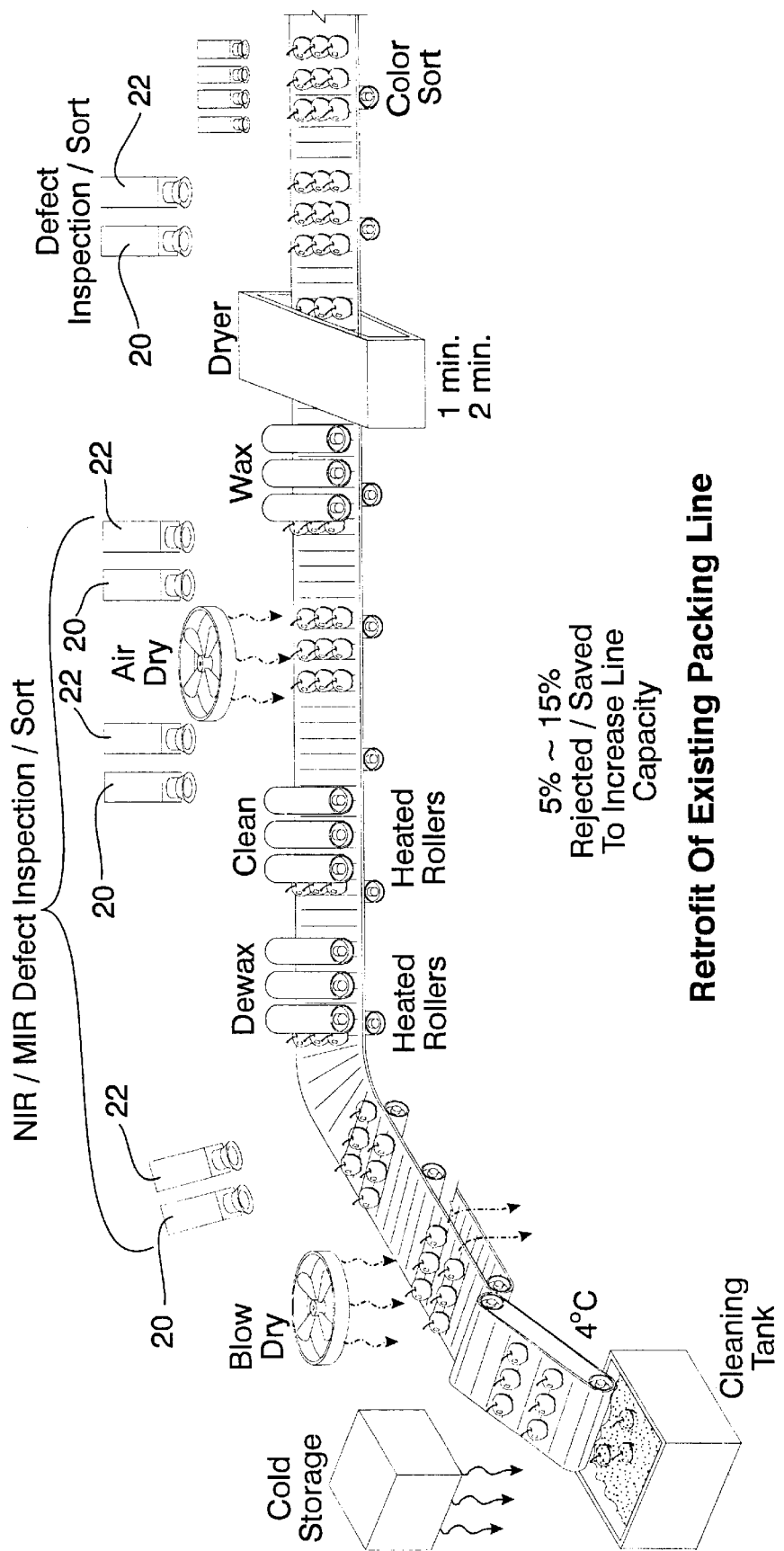

As shown in FIG. 12 a schematic overall operation or item packing system is shown wherein the NIR and MIR cameras and defect detection and discrimination system of the present invention is incorporated along the pack line either just downstream of the cleaning tank and blow dry, in the area of the dewax or clean, just upstream of wax application, or just downstream of the dryer. It is preferred to place the NIR/MIR defect inspection and sort system of the present invention as far upstream as possible so that rejected or sorted items are removed prior to additional processing and thereby reducing cost, increasing line capacity, and the like. Since the defect inspection and sorting system of the present invention relies on a change in temperature to provide a better discrimination of true defects from stem-end, stems, and calyx, it is preferred to use it just downstream of a heating sequence, a heating blow dry, in association with heated rollers or brushes, or downstream of the dryer.

In accordance with the present invention, the particular grader, sorter, separator, or the like, is not limited but it includes kickers, drop bins, pushers, gates, robotic arms, and/or the like.

Thus, it will be appreciated as the result of the present invention, a highly effective improved defect detection and sorting system and apparatus is provided. It is contemplated and will be apparent to those skilled in the art from the preceding description and accompanying drawings that modifications and/or changes may be made in the illustrated embodiments without departure from the present invention.

SEQUENCE LISTING

Not Applicable.

What is claimed is:

1. An apparatus adapted to detect defects in an object and to differentiate between false and true defects, said apparatus comprising:

a first camera adapted to produce a first photograph of said object in the near-infrared range, said first photograph depicting both false and true defects;

a second camera adapted to produce a second photograph of said object in the mid-infrared range, said second photograph depicting only false defects;

imaging means for processing said first and said second photographs to produce a first and a second digital image of said object with said first digital image depicting both false and true defects and with said second digital image depicting only false defects; and, means for logically comparing and contrasting said first and said second digital images to eliminate false defects while maintaining true defects.

2. The apparatus as recited in claim 1, wherein said object comprises irregular exterior features surrounding an internal core and wherein said apparatus includes means for initially treating said object to create a thermal difference between said irregular exterior features and said internal core prior to said first camera.

3. The apparatus as recited in claim 2, wherein said means for initially treating said object comprises a refrigerator.

4. The apparatus as recited in claim 2 wherein said means for initially treating said object comprises a heater.

* * * * *